United States Patent [19]
Nobuta

[11] Patent Number: 5,402,462
[45] Date of Patent: Mar. 28, 1995

[54] X-RAY CT SCANNER

[75] Inventor: Yasuo Nobuta, Tochigi, Japan

[73] Assignee: Kabushiki Kaisha Toshiba, Kanagawa, Japan

[21] Appl. No.: 265,611

[22] Filed: Jun. 24, 1994

Related U.S. Application Data

[63] Continuation of Ser. No. 10,796, Jan. 29, 1993, abandoned.

[30] Foreign Application Priority Data

Jan. 31, 1992 [JP] Japan .................................. 4-015634

[51] Int. Cl.$^6$ .............................................. A61B 6/00
[52] U.S. Cl. ............................................ 378/20; 378/8; 378/205
[58] Field of Search ................. 378/20, 4, 8, 205, 206, 378/208, 209, 95

[56] References Cited

U.S. PATENT DOCUMENTS

| | | | |
|---|---|---|---|
| 3,783,863 | 1/1974 | Kliever ................................ | 378/209 |
| 4,570,264 | 2/1986 | Liebetruth ............................ | 378/20 |
| 4,624,007 | 11/1986 | Muranushi ........................ | 378/20 X |
| 4,789,929 | 12/1988 | Nishimura et al. .................... | 378/20 |

FOREIGN PATENT DOCUMENTS 2-191437  7/1990  Japan .
3-207346  9/1991  Japan .

Primary Examiner—David P. Porta
Attorney, Agent, or Firm—Finnegan, Henderson, Farabow, Garrett & Dunner

[57] ABSTRACT

An X-ray CT scanner, favorable to mass screening, has a gantry in which an X-ray tube radiates an X-ray beam for a patient carrying through an opening for scanning formed therein. The X-ray tube rotates inside the gantry under scanning. The scanner has also an element for reconstructing computed tomography images with using data of the X-ray beam received through the patient. The scanner comprises a couch having a tabletop on which the patient lies down, the tabletop being movable along a longitudinal direction of the couch. Also provided are an element for carrying the tabletop from an initial position through the opening and an element for recognizing a predetermined longitudinal scan range while the tabletop is being carried. Further provided is an element for working the reconstruction element when the scan range is recognized.

43 Claims, 14 Drawing Sheets

X-RAY CT SCANNER

This application is a continuation of application Ser. No. 08/010,796, filed Jan. 29, 1993, now abandoned.

BACKGROUND OF THE INVENTION

The present invention relates to an X-ray CT (computed tomography) scanner, and more particularly to the X-ray CT scanner having an automatic scanning mechanism which covers a series of operational sequences from the beginning to the end of a CT examination, which is especially favorable to mass screening.

Prior to diagnosis with an X-ray CT scanner, an operator places a patient in place on a patient couch and determines desired slicing planes, known as a positioning. A first positioning method uses a positioning light and a second method uses a scanographed image. In the former method, in which a tabletop having a patient is moved by hand, the positioning light is operated to point its light beams at a starting position of desired slicing planes by X-ray scanning. In the latter method, scanography can be made prior to diagnostic scan for obtaining the scanographed image on which desired slicing planes including its starting position can be specified.

After completing the positioning the tabletop is carried along the patient's body axis by means of an automatic sliding mechanism into an opening of a gantry to bring the starting position to an X-ray beam position in the opening. The scan is followed immediately by the tabletop being moved along the body axis.

During the diagnostic scan, the patient is required to stop her or his breathing to eliminate body motion artifacts. An instruction to stop breathing is currently given by an operator's voice or by sequential turn on or turn off of plural LEDs on the gantry.

On completing the diagnostic scan, the tabletop is drawn out and carried back to its initial position in response to an operation by hand, and the patient couch is lowered to bring the patient down.

However, in the above sequence of operations, the operator has to intervene by hand many times between operations directed by a console of the scanner. Such operations by hand include mainly the setting of the patient in place on a couch and the determination of slicing planes. These manual operations form a substantial part of the entire operation and require much operator's work, thus remarkably reducing the efficiency of the X-ray CT scan. This drawback is especially true of mass screening.

On the other hand, giving an instruction to stop patient's respirations by voice tends to result in failure, because the patient does not recognize a necessary time interval of respiration stop for the whole diagnostic scan. Though the above-said LEDs, which sequentially turn on or turn off, helps recognition of the respiration-stop time interval, it is not sufficient because an exact time cannot be shown on the LEDs.

SUMMARY OF THE INVENTION

Accordingly, it is an object of the present invention to provide an X-ray CT scanner which reduces an operator's manual operation and increases the throughput of examination.

Another object of the present invention is to reduce failures of temporary respiration-stop of patients for more increased throughput of examination.

Still another object of the present invention is to supply an X-ray CT scanner which favors mass screening.

Still another object of the present invention is to simplify setting of patients on a couch for further increased throughput of examination.

These and other objects can be achieved according to the present invention, in one aspect, by providing an X-ray CT scanner having a gantry in which an X-ray tube radiates an X-ray beam for a patient carrying through an opening for scanning formed therein, the X-ray tube rotating inside the gantry under scanning, and having an element for reconstructing computed tomography images using data of the X-ray beam received through the patient, the scanner comprising: a couch having a tabletop on which the patient lies down, the tabletop being movable along a longitudinal direction of the couch; an element for carrying the tabletop from a predetermined initial position in the longitudinal direction through the opening; an element for recognizing a predetermined scan range in the longitudinal direction while the tabletop is being carried by the carrying element, the scan range corresponding to a desired scanning region; and an element for working the recognizing element when the recognizing element recognizes the scan range.

In another aspect according to the present invention, there is also provided an X-ray CT scanner in which the recognizing element generates start information and end information corresponding to the scan range. The X-ray CT scanner further comprises an element for automatically stopping travel of the tabletop in response to the end information and an element for automatically returning the tabletop to its initial position after the tabletop was stopped.

In still another aspect according to the present invention, there is also provided an X-ray CT scanner further comprising an element for informing the patient of temporary discontinuation of respiration under scanning, through counting down and/or displayed times and a voice message.

BRIEF DESCRIPTION OF THE DRAWINGS

The accompanying drawings, which are incorporated in and constitute a part of this specification, illustrate embodiments of the present invention and, together with the description, serve to explain the principles of the present invention. In the drawings.

DESCRIPTION OF THE PREFERRED EMBODIMENTS

Embodiments of the present invention will now be described with reference to the accompanying drawings.

A first embodiment will now be described according to FIGS. 1 through 7A and 7C.

Figure 1:
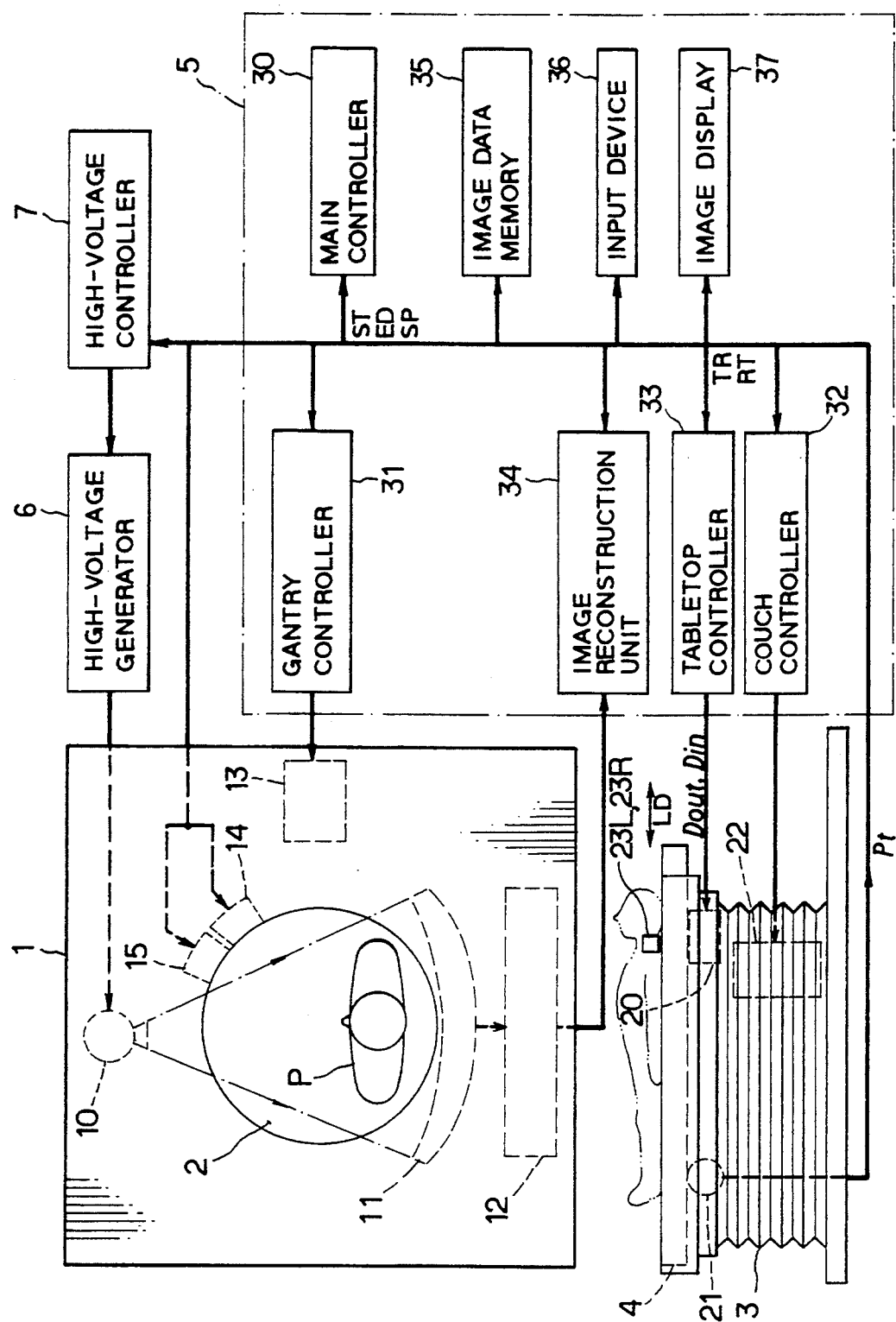
FIG. 1 shows in block form an X-ray CT scanner of a first embodiment according to the present invention.

FIG. 1 is a block diagram schematically representing the construction of an X-ray CT scanner. The X-ray CT scanner shown therein comprises a gantry 1 having an opening 2 for X-ray scanning, a patient couch 3 having a tabletop 4 on which a patient P lies as an object being diagnosed, a console 5 for entire control, and a high-voltage generator 6 and a high-voltage controller 7 for generating high voltage.

An X-ray tube 10 is incorporated rotatably in the gantry 1 and radiates X-ray beams for the patient P placed in the opening 2. The X-ray beams transmitted through the patient P are received by an X-ray detector 11, installed also rotatably at the opposite side of the opening 2 in the gantry 1, for converting the received X-ray beams into electrical currents. The electrical currents are supplied to a data acquisition system 12, placed in the gantry 1, for converting the detected analog currents into digital quantities.

A gantry driving mechanism 13 is provided in the gantry 1. The gantry driving mechanism 13, which controls the movement of the gantry 1, works by driving signals supplied from the console 5. Further, on a dome wall of the opening 2, there are provided a voice generator 14 for giving patient P instructions in regard to a temporary discontinuation of respiration of the patient P and a time display unit 15 showing a time interval of the temporary discontinuation of respiration necessary for designated diagnostic scanning. For example, the voice generator 14 has a voice synthesizer and the time display unit 15 has a digital clock which counts down, both of which work in response to signals from the console 5. The time display unit 15 is able to be seen by the patient under X-ray scanning. Therefore, the attachment position of the time display unit 15 is not limited to the gantry 1 as described above, and it is possible to attach the time display unit 15 to the couch 3 or even to a scanner room.

By means of a tabletop driving unit 20 installed in the couch 3, the foregoing tabletop 4 is able to be horizontally slidable along its longitudinal direction LD, that is, the direction of a patient's body axis. The tabletop driving unit 20 receives driving signals Dout and Din supplied from the console 5. Traveling positions of the tabletop 4 are detected by a tabletop position detector 21 placed in the couch 3, and a detected position signal Pt is provided to the console 5. The tabletop position detector 21 consists of, for example, a rotary encoder. Moreover, the tabletop 4 can be lowered and lifted by a couch driving unit 22. The couch driving unit 22 works in response to driving signals from the console 5.

Figure 2:
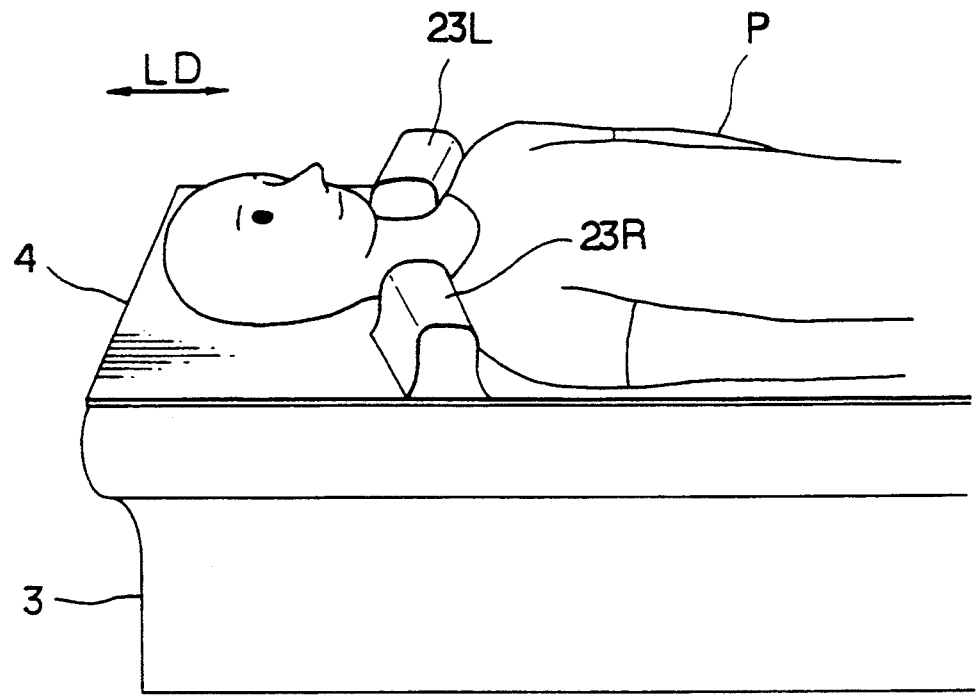
FIG. 2 shows an illustration for explaining body positioning pads and a patient.

In this embodiment, as shown in FIG. 2, a pair of body positioning pads 23R and 23L serving as body positioning means of the present invention, each being formed into an approximate box shape, are fixedly attached at appropriate positions on both the longitudinal end sides of the tabletop 4. Thus, the patient P is to be laid on the tabletop 4, with her or his shoulders attached to the pads 23R and 23L (refer to FIG. 2). One purpose of the body positioning by the pads 23R and 23L is to specify approximate patient lying positions on the tabletop 4 and to avoid excessive changes in scan range. Accordingly, the pads 23R and 23L indirectly specify a shoulder position that corresponds to a standard position of the present invention. As a result, the scan range of each patient can exist in a predetermined allowable range along the body axis direction LD.

Figure 3:
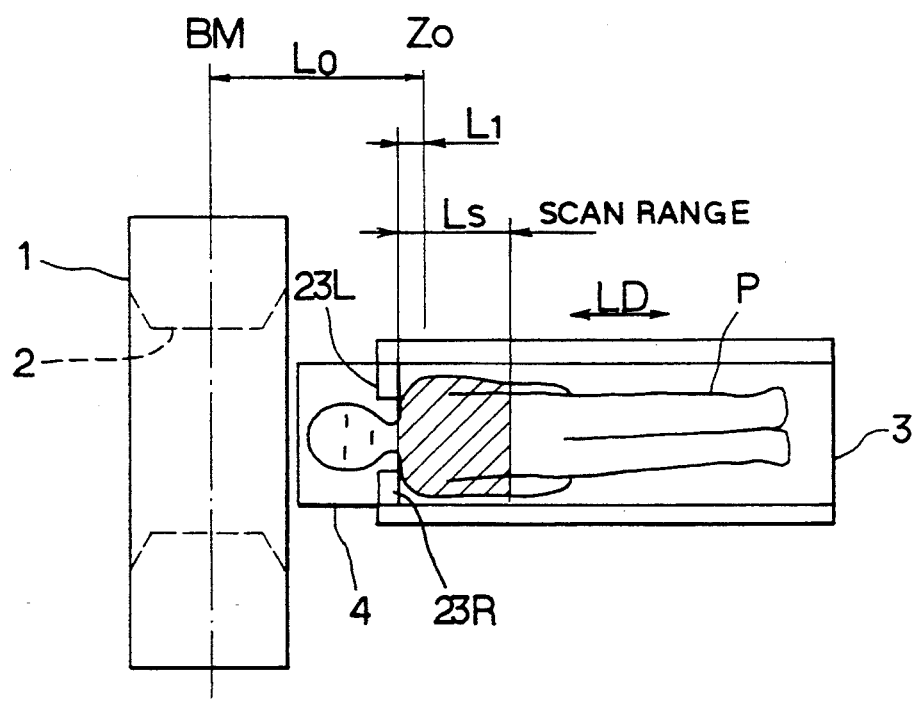
FIG. 3 represents an example of a layout for a scan range.

A target scan field in this embodiment is for the lungs of patients, so the scan range described above is determined to have a length of Ls ranging from the position of the pads 23L and 23R toward her or his feet, as shown in FIG. 3.

A point of reference Zo of the patient couch 3 in the body axis direction LD is preset, as shown in FIG. 3. Moreover, there is a distance Lo between an X-ray beam position BM in the gantry 1 (in other words, a slicing position by X-ray beams) and the point of reference Zo. There is also a difference of L1 in longitudinal length between the reference point Zo and the position of the pad 23L and 23R, when the tabletop 4 being positioned at its initial point.

In the console 5, there is provided an main controller 30, a gantry controller 31, a couch controller 32, a tabletop controller 33, an image reconstruction unit 34, an image data memory 35, an input device 36, and an image display 37, which are interconnected with each other. The input device 36 is, for example, a keyboard and is used by an operator. The main controller 5 is also connected to the high-voltage controller 7.

Figure 4:
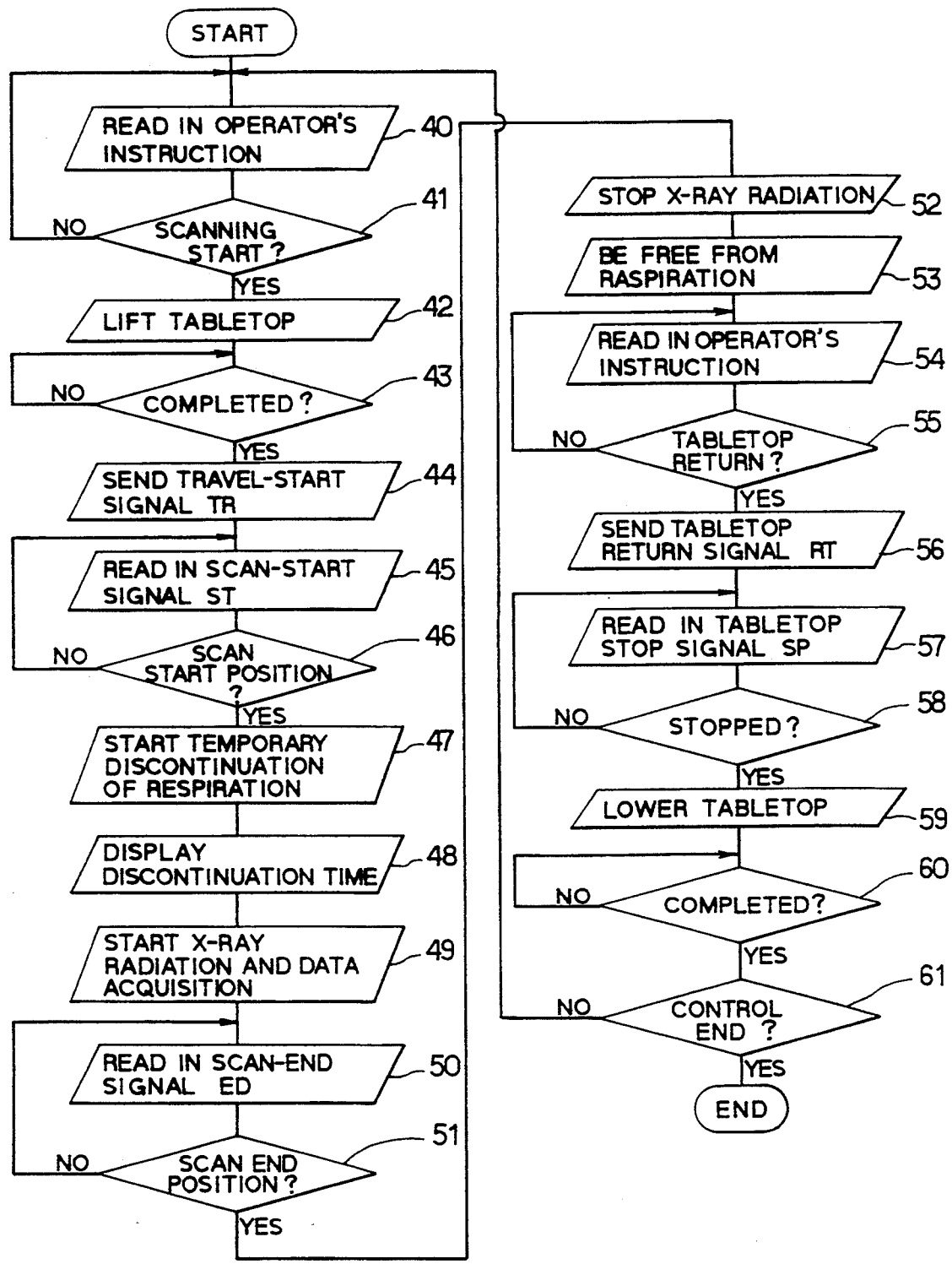
FIG. 4 represents a flowchart showing a procedure performed in a main controller.

The main controller 30 is in charge of the entire control including a series of processes of a designated scan shown in FIG. 4.

The gantry controller 31, the couch controller 32, the tabletop controller 33, and the high-voltage controller 7 are under control of the main controller 30. When receiving instruction signals from the main controller 30, the gantry controller 31 sends driving signals to the gantry driving mechanism 13 in order to control movement of the gantry 1. Also when receiving instruction signals from the main controller 30, the couch controller 32 sends driving signals to the couch driving unit 22 to adjust the height of the couch 3. The tabletop controller 33, which communicates with the main controller 30, carries out a series of processes shown in FIG. 5, thus sending the driving signal Dout or Din to the tabletop driving unit 20. Moreover, according to instruction signals from the main controller 30, the high-voltage controller 7 sends instruction signals to the high-voltage generator 6, so that predetermined high-voltage is supplied to the X-ray tube 10.

On the other hand, the digital data converted by the data acquisition system 12 are sent to the image reconstruction unit 34 in the console 5 for forming computed tomography image data. The detected signal Pt by the tabletop position detector 21 is also sent to the tabletop controller 33 in the console 5 for recognizing the tabletop positions, namely, the patient positions in the body axis direction LD.

Next, according to FIG. 4, the processing of the main controller 30 will then be explained.

At Step 40 in FIG. 4, the main controller 30 tries to read in an instruction of starting scanning through the input device 36 from an operator. Then at Step 41, according to the reading-in result at Step 40, it is determined whether or not the start of the scanning is instructed. If the determination is NO (i.e., the start of the scanning has not been instructed yet), the processes at Steps 40 and 41 will be repeated. But if the determination is YES (i.e., the start of the scanning is instructed), then processes at Steps 42 and 43 follow.

At Step 42, an instruction lifting the patient couch 3 from its predetermined lowered height to its predetermined diagnostic height is sent to the couch controller 32. Then at Step 43, it is determined whether or not the lift of the patient couch 3 has been completed. The determination is performed according to a reply from the couch controller 32 and continued until the lift has completed.

When the lift has been completed, processes of Steps 44 to 46 will then follow. At Step 44, a travel-start signal TR representing the start of travel of the tabletop 4 along the body axis LD is sent to the tabletop controller 33. Then at Step 45, a scan-start signal ST representing that the tabletop 4 reaches a predetermined scan start position is tried to be read in from the tabletop controller 33. At Step 46, it is determined whether or not the tabletop 4 has reached the predetermined scan start position. If the determination is NO (i.e., the scan start position has not been reached yet), the processing returns to Step 45.

When the determination is YES at Step 46, the processes of Steps 47 to 49 will follow in turn. First, at Step 47, an instruction representing a temporary discontinuation of respiration is sent automatically from the main controller 30 to the voice generator 14. Thus, the voice generator 14 says a preset voice message to request the patient P to begin her or his temporary stop of respiration.

Then at Step 48, another instruction starting countdown of a time interval of the temporary discontinuation of respiration is also sent to the display unit 15. In response to the instruction, the display unit 15 first displays a maximum of the time interval in a digital value and then begins to count down, while displaying the countdown values. Namely, when the countdown comes to the displayed figure zero, the patient can start respiration.

Then at Step 49, still other instructions, which can initiate X-ray radiation from the X-ray tube 10 and data acquisition by data acquisition system 12, are given to the high-voltage controller 7, the gantry controller 31 and the image reconstruction unit 34. As a result, scanning for diagnosis starts according to a specified scan mode, for example, a helical scan. Of course, the scanning is not limited to the helical scan.

After the start of the above scanning, the main controller 30 waits with repeating Steps 50 and 51. At Step 50, a scan-end signal ED representing that the tabletop 4 reaches a predetermined scan end position is tried to be read in from the tabletop controller 33. At Step 51, whether or not the tabletop 4 has reached a predetermined scan end position is determined. If the determination is NO (i.e., the scan-end position has not been reached yet), the processing is repeated through Steps 50 and 51.

When the determination is YES at Step 51, the processing goes on to Steps 52 and 53. Stoppage of the X-ray radiation and data acquisition are ordered at Step 52. Then an instruction with regard to the release from the temporary discontinuation of respiration is given from the main controller 30 to the voice generator 14 at Step 53. Hence, the voice generator 14 generates a voice message saying that the patient can again begin breathing.

Then, the main controller 30 waits for an instruction from the operator as to whether to repeat Steps 54 and 55. These Steps can decide return timing of the tabletop 4 according to the operator's will. Namely, the instruction from the operator is read in, and if the tabletop 4 should be returned or not is determined. If the determination is YES at Step 55, a tabletop return signal RT is sent to the tabletop controller 33 at Step 56.

Steps 54 and 55 are omittable, if necessary. If the omission is made, the tabletop 4 will be automatically returned by the instruction at Step 56.

Then at Step 57, a tabletop stop signal SP, representing the return to and stop at its initial position of the tabletop 4, is read in from the tabletop controller 33. At Step 58, whether or not the tabletop 4 has stopped is determined according to the tabletop stop signal SP.

If the determination is YES at Step 58, the height of the couch 3 is ordered to be lowered by giving a corresponding instruction to the couch controller 32 at Step 59. Then, in accordance with a reply from the couch controller 32, it is determined whether or not the height of the couch 3 has been adjusted to the initial lowered position at Step 60. When the height adjustment of the couch 3 has been completed, whether the entire control should be ended or not is determined at Step 61. If the determination is NO, the processing by the main controller 30 returns to Step 40.

Next, according to FIG. 5, the processing of the tabletop controller 33 will be explained, which is to be carried out in parallel with the foregoing processing of the main controller 30.

Figure 5:
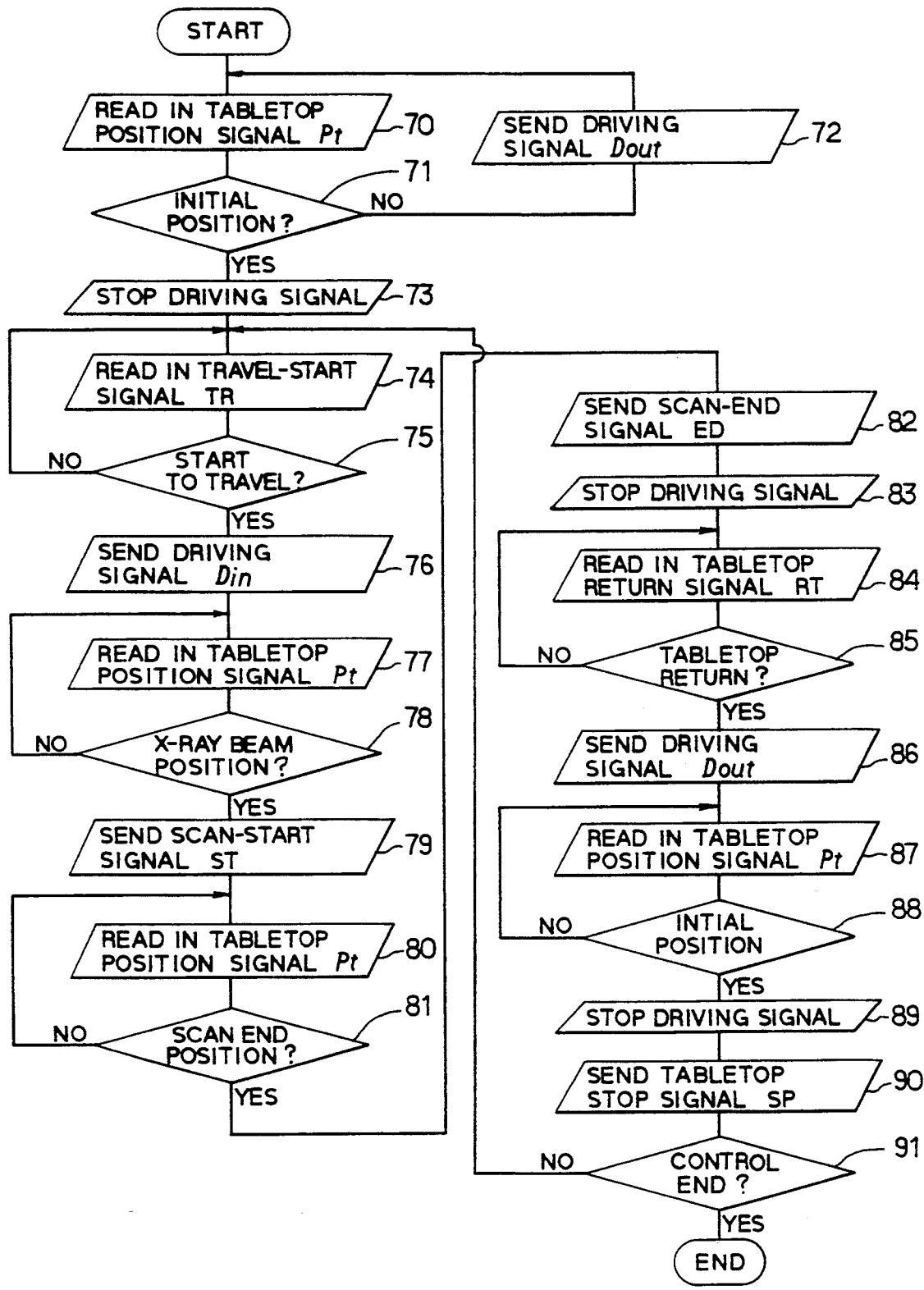
FIG. 5 represents a flowchart showing a procedure performed in a tabletop controller.

In the first stage after power on, by Steps 70 to 73 in FIG. 5, the tabletop controller 33 brings the position of the tabletop 4 to its predetermined one in the body axis direction LD. That is, at Step 70, the position signal Pt detected by the tabletop position detector 21 is read in, and at Step 71, whether the tabletop 4 exists at its initial position or not is determined. If the determination is NO, a driving signal bout is sent to the tabletop driving unit 20 at Step 72, so that the tabletop 4 moves outward from the opening 2 along the body axis direction LD and comes back to the limit of the feet-side end of the couch 3 as the initial position. If the determination is YES at Step 71, the driving signal bout is stopped at Step 73. As a result, whenever scanning for diagnosis is performed, the tabletop 4 can surely travel from its initial position.

Then the processing of Steps 74 and 75 follows. At Step 74, the tabletop controller 33 tries to read in the travel-start signal TR from the main controller 30 (refer to Step 44 in FIG. 4). At Step 75, based on the reading-in result, it is determined whether or not tabletop 4 should start to travel for scanning. When the determination is NO, it is not ready yet for an operator to start scanning, thus the processing will be returned to Step 74. When the determination is YES at Step 75, it has been recognized that it is time for start of scanning.

Then, at next Step 76, the tabletop controller 33 sends the driving signal Din to the tabletop driving unit 20 in order that the tabletop 4 start to travel inward through the opening 2.

While the tabletop 4 is travelling, the tabletop position signal PT detected by the tabletop position detector 21 is read in at Step 77. Using the reading-in signal, it is determined whether or not the position of the body positioning pads 23L and 23R reaches the X-ray beam position BM at Step 78. In detail, this determination is made by a calculation such that a travel distance value Sa measured at Step 77 is equal to "Lo-L1 (or "Lo+L1")". If, in a certain embodiment L1=0, "Sa=Lo" may be used.

If the determination is NO at Step 77, the position of the body positioning pads 23L and 23R has not yet reached the X-ray beam position BM, and the processing of Steps 77 and 78 are repeated. But a determination of YES at Step 78, a scan-start signal ST is sent to the main controller 30 at Step 79 (refer to Step 45 in FIG. 4).

After this, at Step 80, the tabletop position signal Pt is read in and a scanned length Sb, which have finished so far, is calculated. It is determined then at Step 81 whether or not the calculated scanned length Sb equals a preset value Ls of the scan range. These Steps 80 and 81 are repeated until "Sb=Ls".

When the feet-side end of the scan range Ls reaches the X-ray beam position BM in the gantry 1, the determination YES is obtained at Step 81. Hence, at Step 82, a scan-end signal ED is sent to the main controller 30 to indicate an end of the tabletop travel (refer to Step 50 in FIG. 4). At Step 83, the driving signal Din to the tabletop driving unit 20 is stopped.

Then, the tabletop return signal RT (refer to Step 56 in FIG. 4) is read in at Step 84, and it is determined whether the table 4 should be returned at Step 85. When the determination is YES at Step 85, the driving signal Dout is then sent to the tabletop driving unit 22 to draw the tabletop 4 back at Step 86. By this instruction, the tabletop 4 begins to return outward to its initial position.

While the tabletop 4 is returning, the tabletop position signal Pt is examined (Step 87) and it is determined if the tabletop 4 has returned to the initial position (Step 88). When the return of the tabletop 4 has completed (i.e., the determination is YES at Step 88), the foregoing driving signal Din is stopped at Step 89. After this, at Step 90, a tabletop stop signal SP (refer to Step 57 in FIG. 4) is sent to the main controller 30 to indicate the completion of the tabletop return.

Finally, at Step 91, the tabletop controller 33 determines that the processing should be ended or not according to, for instance, an operator's instruction. If a next patient is to be examined, the processing returns to Step 74.

In the foregoing explanation, the data acquisition system 12 and the image reconstruction unit 34 form a CT image reconstructing means of the present invention. Step 44 in FIG. 4 and Steps 74 to 76 in FIG. 5 form carrying means of the present invention. Further, the tabletop position detector 21, Steps 45, 46, 50, 51, and Steps 77 to 82 are combined to compose recognizing means of the present invention. Steps 77 and 78 especially correspond to the main part of a sensor means of the present invention. Steps 49 and 52 correspond to controlling means of the present invention.

Furthermore, automatic stopping means of the present invention are composed of Step 83 in FIG. 5, and automatic returning means are composed of Steps 54 to 56 in FIG. 4, Steps 84 to 89 in FIG. 5, and the tabletop position detector 21. Automatic lowering/lifting means are composed of Steps 57 to 60 and 42, 43 in FIG. 4 and Step 90 in FIG. 5. Also, informing means of the present invention are formed by the voice generator 14, the time display unit 15, and Steps 47, 48 and 53.

According to the above-said processing, an example of entire semi-automatic operation is explained using FIGS. 6 and 7A to 7C.

First, with the couch 3 being lowered to its initial height, a patient lies down on the tabletop 4 under the operator's instruction. The operator takes care that the patient touches the body positioning pads 23R and 23L at the patient's shoulders, as shown in FIG. 2.

Figure 6:
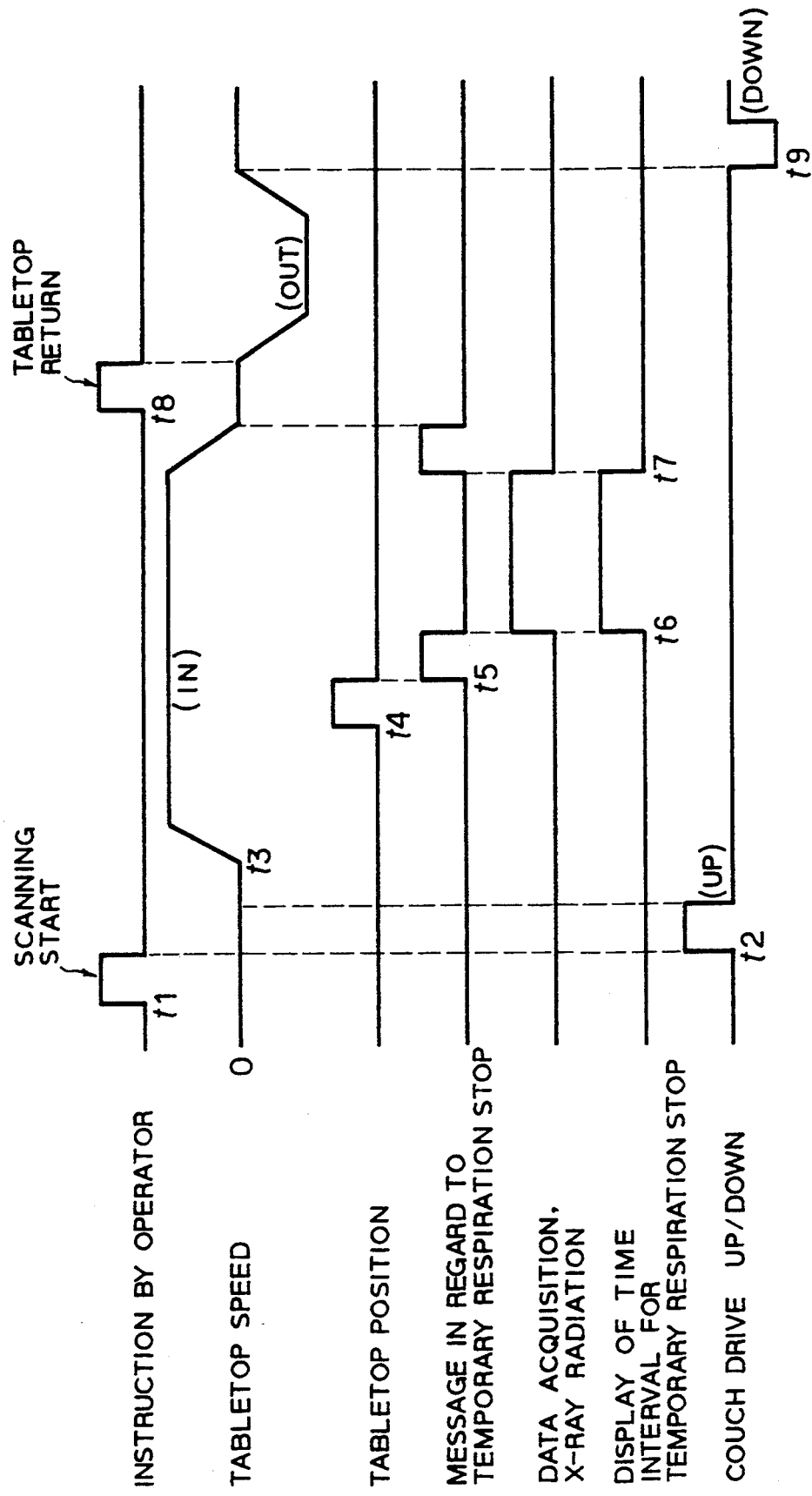
FIG. 6 shows a timing chart of the first embodiment.

After completing preparation, including registration of the patient P, the operator instructs the scanner to start an automatic X-ray CT scanning through the input device 36 at a time t1 shown in FIG. 6. In response to this instruction, the tabletop 4 is lifted vertically to the diagnostic position by the elongation of the couch 3 (refer to a time interval t2 to t3 in FIG. 6).

Figure 7A:
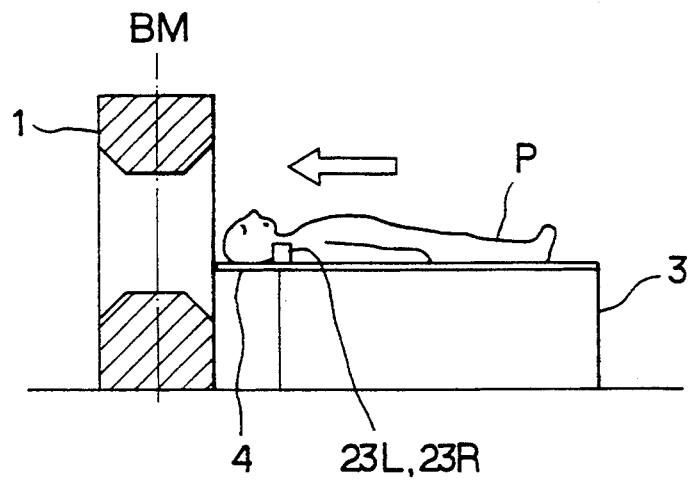
FIGS. 7A to 7C each show travel of a tabletop in the first embodiment.

Then the travel-start signal TR is sent from the main controller 30 to the tabletop controller 33 (see Step 44 in FIG. 4 and Step 74 in FIG. 5). By this sending the signal TR, the main controller 30 waits for the scan-start signal ST, whereas the tabletop controller 33 causes the tabletop 4 to travel horizontally inward for the scanning from its initial longitudinal position toward the opening 2, as shown in FIG. 7A.

Figure 7B:
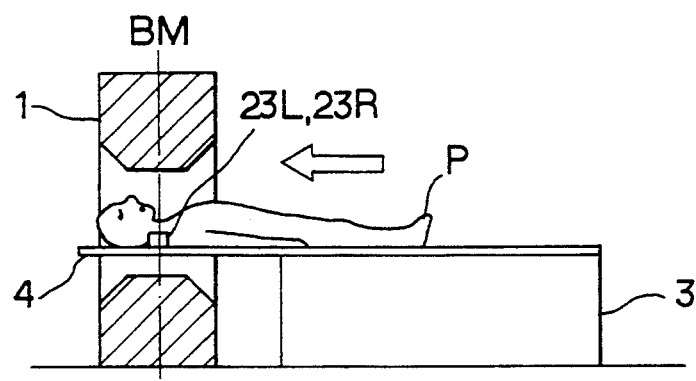

As shown in FIG. 7B, when the position of the body positioning pads 23L and 23R reaches the X-ray beam position BM at a time t4, the scan-start signal ST is sent back to the main controller 30 (see Steps 78 and 79 in FIG. 5 and Step 45 in FIG. 4).

By this signal-sending, a temporary discontinuation of breathing is instructed automatically through a voice message at a time t5, and then X-ray radiation and data acquisition by a helical scan mode is started at a time t6, as shown in FIG. 6. At the same time, a time interval of temporary discontinuation of respiration needed for the scanning (for instance, 10 seconds) is displayed on the time display unit 15 and is counted down in each time synchronized with the scanning (see Steps 47 to 49).

Figure 7C:
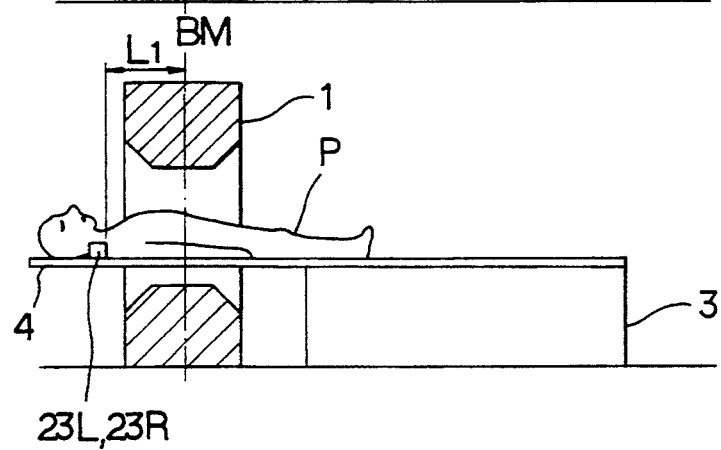

The above scanning state continues until a time t7, when the tabletop 4 is deeply through the opening 2 and the end of the scan range preset value Ls has reached the X-ray beam position BM as shown in FIG. 7C. At this time, the scan-end signal ED is sent from the tabletop controller 33 to the main controller 30 (see Step 82 in FIG. 5 and Step 50 in FIG. 4). Therefore, the X-ray radiation is stopped and then the temporary stop of respiration which has been forced so far is now released. At this time, the countdown value is also zero on the display unit 15.

The tabletop 4 is stopped and the instruction of tabletop return signal RT is awaited (See Step 56 in FIG. 4 and Step 84 in FIG. 5). When the operator gives a return instruction by hand at a time t8, the tabletop 4 starts to return outward. When the tabletop 4 has returned to its initial longitudinal position, it is stopped and the tabletop stop signal SP is communicated (See Step 90 in FIG. 5 and Step 57 in FIG. 4). At a time t9, the couch 3 is lowered so that the patient P can get off the couch 3.

If necessary, e.g., in a mass screening, a next patient lies on the lowered couch 3, and the aforementioned procedure is repeated.

As has been described, the present embodiment provides a totally new way of X-ray CT scanning. While scanning a patient, a desired target scan range is designated. In other words, scanning can be done immediately after the registration of a patient, without carrying out particular troublesome scan positioning.

Therefore, according to the present embodiment, operation work for an operator and scanning times are both largely reduced as compared with the conventional scanning. It is simpler and easier to position a patient body on the couch 3 thanks to the body positioning pads, and it is unnecessary to take positioning images prior to scanning. Moreover, operation by hand is limited to a minimum. All these factors combine to result in increasing a throughput of X-ray scanning and in reducing a proportion of troublesome operation.

The above advantages offer an X-ray CT scanner most favorable to mass screening such as for lung cancer, because X-ray scanning is repeated on a same target scan field for many people.

In addition, the voice message and the displayed countdown time, both of which are for a temporary respiration-stop, relieve patients from worrying about the temporary respiration-stop and reduce failures in the action. Thus, a higher quality CT image can be obtained. Also the X-ray exposure to a patient is largely reduced, as scanography is unnecessary.

In this embodiment, the scan range may be judged by utilizing profile data of the lung field in the body axis direction LD, the profile data being obtained in parallel with the foregoing computed tomography image data by a mechanism according to the prior art.

The scan range can be judged by traveling time of the tabletop instead of the traveling distance of it. Further, if the steps of 54 and 55 are omitted, the tabletop may be returned to its initial position immediately after the stop at the end position of the scan range. Still further, the synthesized voice message for the temporary discontinuation of respiration can be replaced by an operator's voice, which should be given timely. Also it is possible to substitute a message conveyed by light signals for the voice message described above.

In addition, the body positioning means of the present invention is not limited to the body positioning pads described above, and may be changed in number, shape, and attached position in accordance with a scanning desired. For example, marks including lines painted on the tabletop are acceptable. If patient bodies are always laid on a predetermined position on the tabletop, the pads described above can be omitted.

Figure 8:
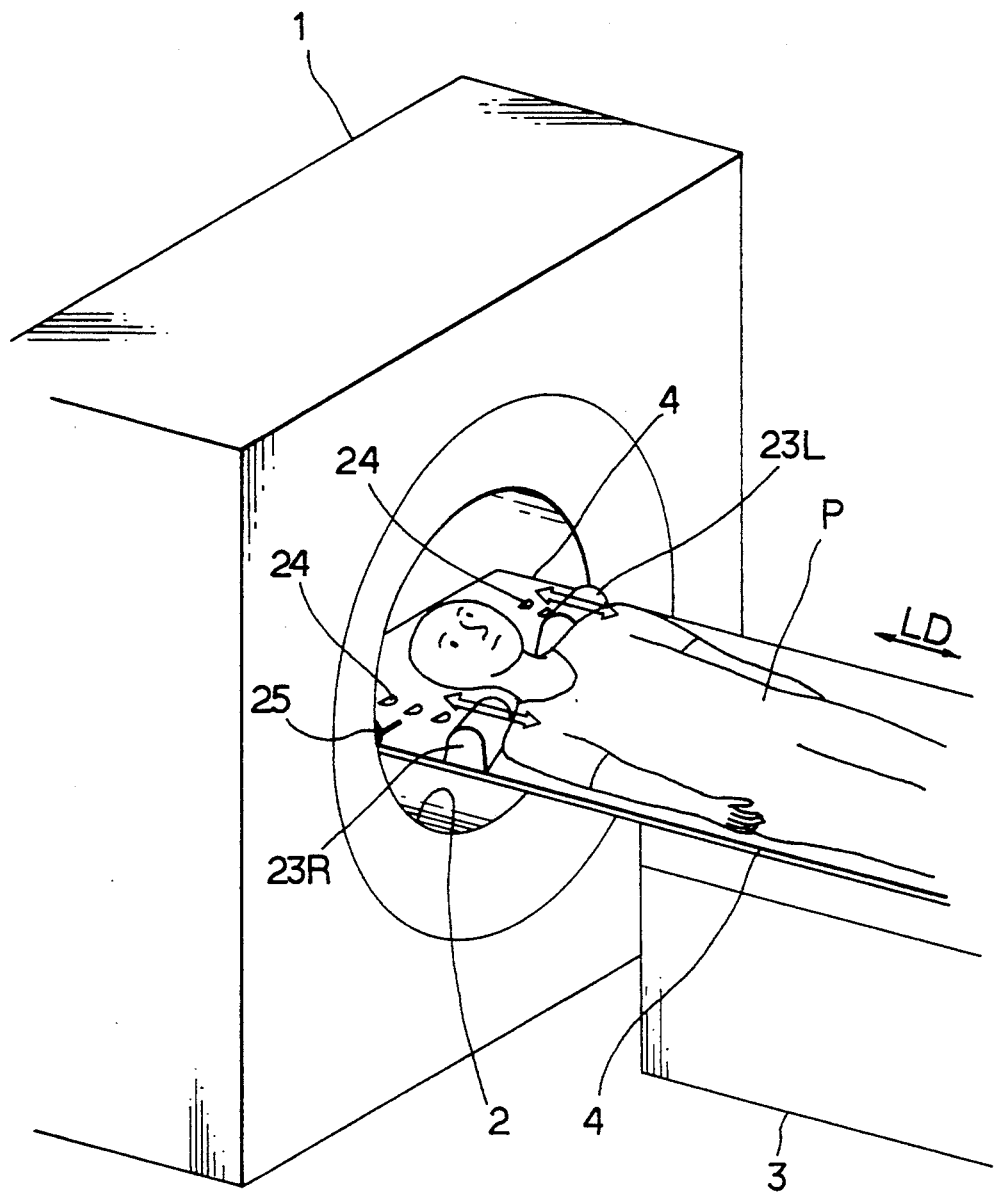
FIG. 8 shows an X-ray CT scanner of a second embodiment according to the present invention.

A second embodiment of the present invention will now be described according to FIG. 8.

This embodiment relates to improvement of patient's body positioning. In this embodiment, as shown in FIG. 8, a pair of body positioning pads 23R and 23L, each being formed into an approximate box shape, are movably attached on the both longitudinal end sides of the tabletop 4. Furthermore, the body positioning pads 23R and 23L have fitting rods and can be moved by a operator along the body axis direction LD by selecting one pair of holes 24 . . . 24 inserted by the fitting rods, the holes 24 . . . 24 being formed along the longitudinal end sides on the tabletop 4 as shown in the figure. The operator places the pads 23L and 23R to a correct position for patients of various heights.

Thus, the patient P lies on the tabletop 4, with her or his shoulders touching the pads 23R and 23L, the position of which is suitably selected by the operator. One purpose of the body positioning by the pads 23R and 23L is to specify approximate patient lying positions on the tabletop 4 and to avoid excessive changes in scan range.

As a result, the scan range of each patient can exist in a predetermined allowable range along the body axis direction LD.

However, the scan-start position is changed. Therefore a touch sensor 25 serving as a sensor means of the present invention is placed on an outer dome wall of the opening 2, as shown in FIG. 8, to detect the arrival of the body positioning pad 23L by touch. A detected signal by the touch sensor 25 is supplied to the tabletop controller 33 and is used to recognize a position corresponding to the scan-start position at Steps 77 and 78 in the processing of FIG. 5.

Thus, this embodiment also offers the same advantages as those in the first embodiment. Besides, the scanner here is more advantageous when the heights of patients differ.

In this embodiment, instead of the touch sensor 25, a photosensor may be placed on the dome wall of the opening 2.

A third embodiment of the present invention will next be explained according to FIGS. 9 through 14A and 14C. The purpose of the third embodiment is to simplify a scanning operation. In this embodiment, the same construction components and processes as the foregoing first embodiment are described using the same references as those for simplification and omission of double explanations.

Figure 9:
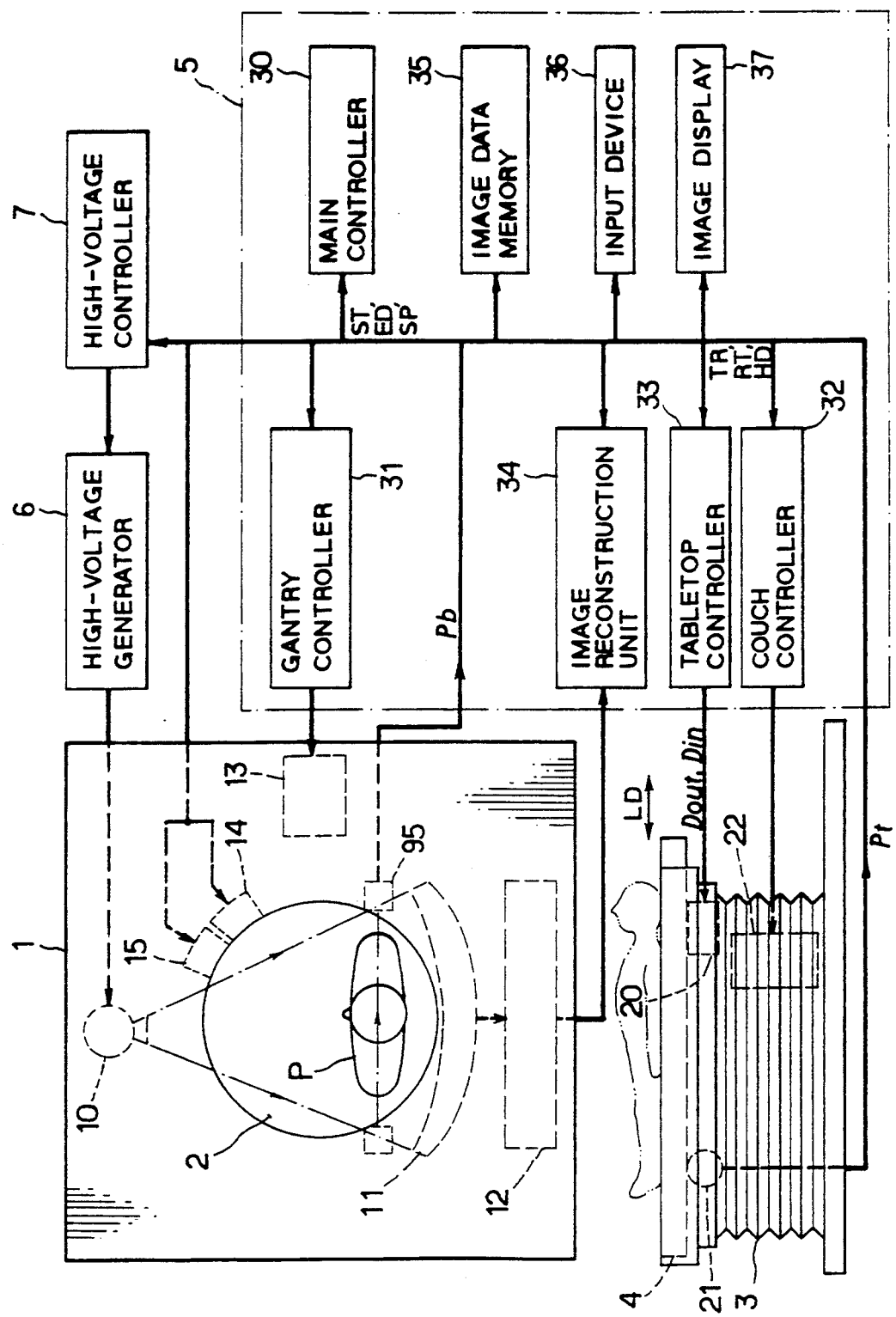
FIG. 9 shows in block form an X-ray CT scanner of a third embodiment according to the present invention.

As shown in FIG. 9, a photosensor 95 serving as a detection mechanism of the present invention is placed. The position of the photosensor 95 is fixed such that a light beam from the photosensor 95 travels across the opening 2 at a longitudinal position apart from the X-ray beam position BM by a predetermined distance Lx (refer to FIG. 10). The output signal Pb from the photo sensor 95 is supplied to the tabletop controller 33 in the console 5.

In this embodiment, a target scan field is for a patient's lungs. For scanning the lungs, a scan range L1 in the body axis direction LD is given as shown in FIG. 2. That is, a length La from the top of the patient's head is designated as a non-scanning range and successively to this range La, the scan range L1 is designated. The length L1 is large enough to cover most patients, even when the patients lie on an approximate lying range on the couch 3.

Figure 11:
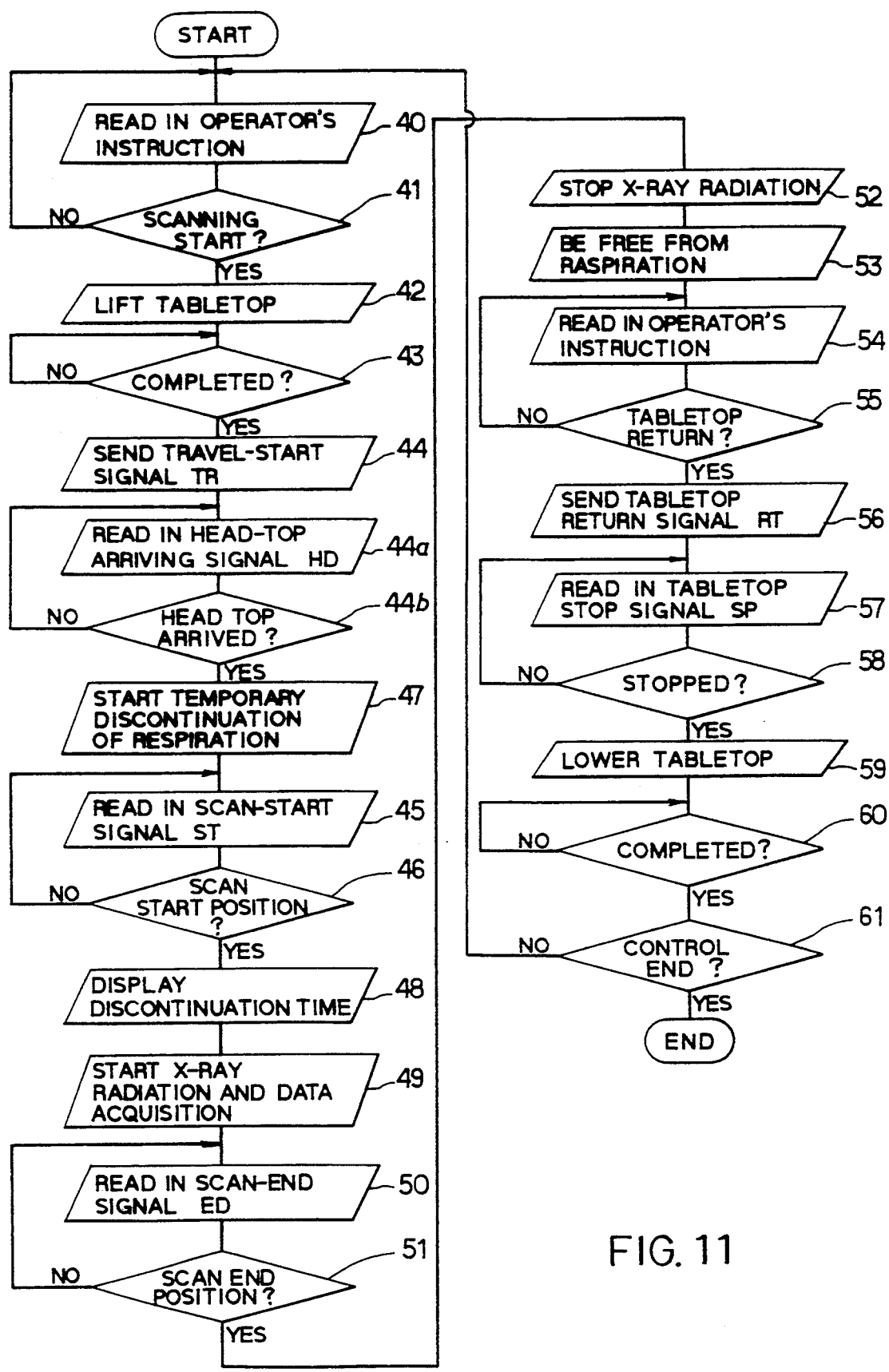
FIG. 11 represents a flowchart showing a procedure performed in a main controller in the third embodiment.
Figure 12:
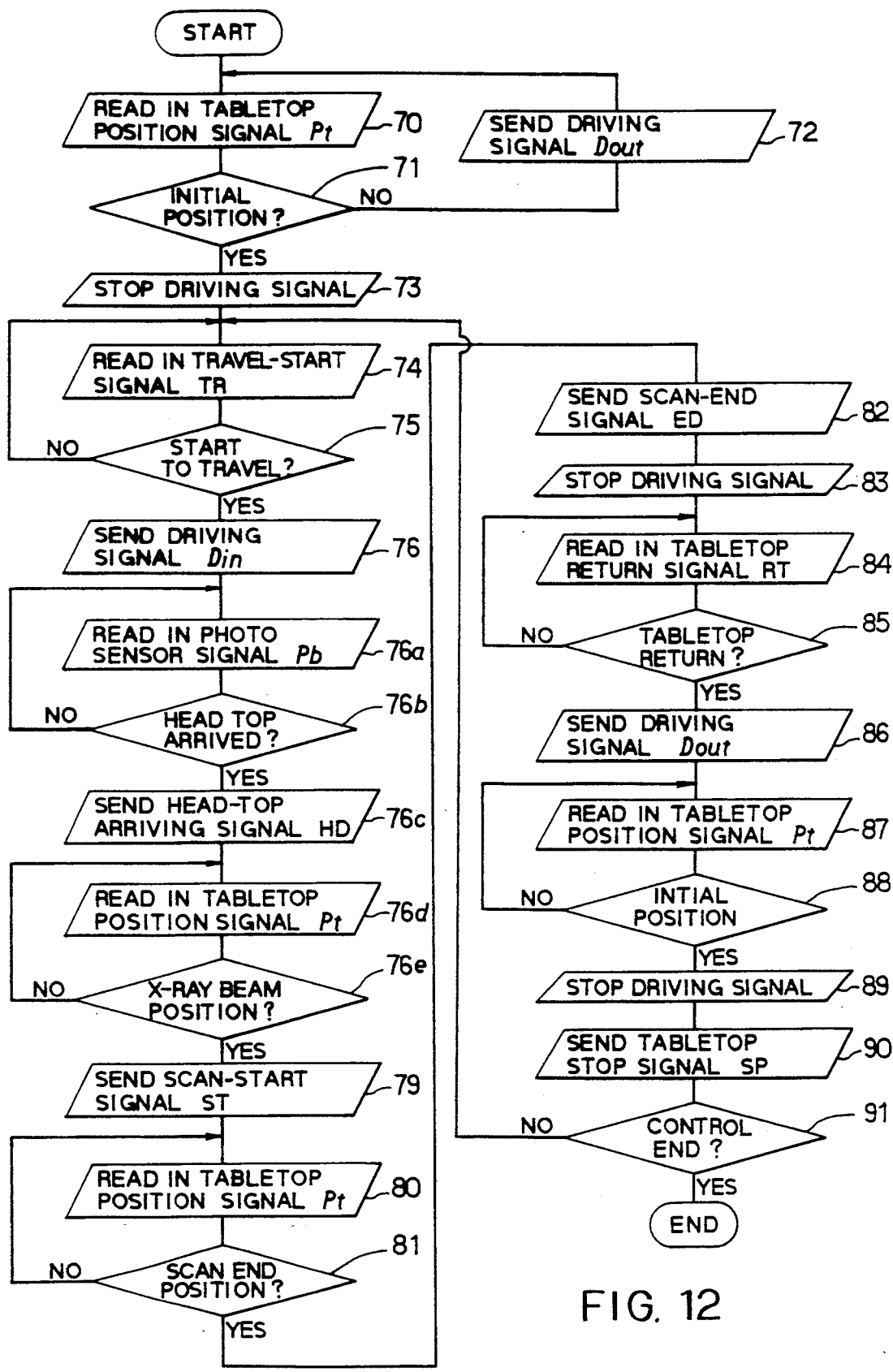
FIG. 12 represents a flowchart showing a procedure performed in a tabletop controller in the third embodiment.

The main controller 30 and tabletop controller 33 in the console 5 perform a series of processes shown in FIG. 11 and a series of processes shown in FIG. 12 individually.

In the processes of FIG. 11 performed by the main controller 30, Steps 40 to 44 are the same as those in FIG. 4. After Step 44, the processing goes on to Step 47 through Steps 44a and 44b. On the way, at Step 44a, an arriving signal HD, representing the arrival of the head top (i.e., a standard position of the present invention) of a patient P to the position of the photo sensor 95, is read in from the tabletop controller 33. Then at Step 44b, it is determined whether the head top has arrived at the predetermined position Lx. When the determination is YES at Step 44b, then Step 47 is processed where a temporary discontinuation of respiration is ordered.

After this, the processing goes on to Step 48 through Step 45 and Step 46 in turn. That is, the temporary stop of respiration here is instructed prior to the input of the scan-start signal ST mentioned before.

The processing at Steps 49 to 61 is the same as those in FIG. 4.

On the other hand, in the processes of FIG. 12 performed by the tabletop controller 33, Steps 70 to 76 are the same as those in FIG. 5. After driving the tabletop 4 for X-ray scanning at Step 76, the tabletop controller 33 will carry out in turn Steps 76a to 76e, before Step 79.

That is, the output signal Pb from the photosensor 95 is read in at Step 76a, and at Step 76b it is determined whether or not the head top of the patient has arrived at the predetermined position Lx. When the head top of the patient reaches the position Lx, the output signal Pb is, for example, stopped. This detection of arrival of the head top allows the determination of YES at Step 76b, thus following to Step 76c. At Step 76c, the arriving signal HD (refer to Step 44a in FIG. 11) is sent to the main controller 30.

Then at Step 76d, the position detection signal of the tabletop Pt is read in and its position is memorized. At Step 76e, it is determined whether or not a predetermined longitudinal length "Lx+La" has been passed after the above arrival of the head not the position Lx. If the determination is NO at Step 76e, it is too early to start scanning. So the processing of the Steps 76d and 76e is repeated. In contrast, a determination of YES at Step 76e means that the start position of the scan range L1 has arrived at the X-ray beam position BM and it is time to start scanning.

Then at Step 79, the scan-start signal ST (refer to Step 45 in FIG. 11) is sent to the main controller 30. Further, Steps 80 to 91 follow as shown in the figure, those of which are the same processing as the previous ones.

Next, an example of the entire automatic scanning will be described according to FIGS. 13 and 14A through 14D.

Figure 13:
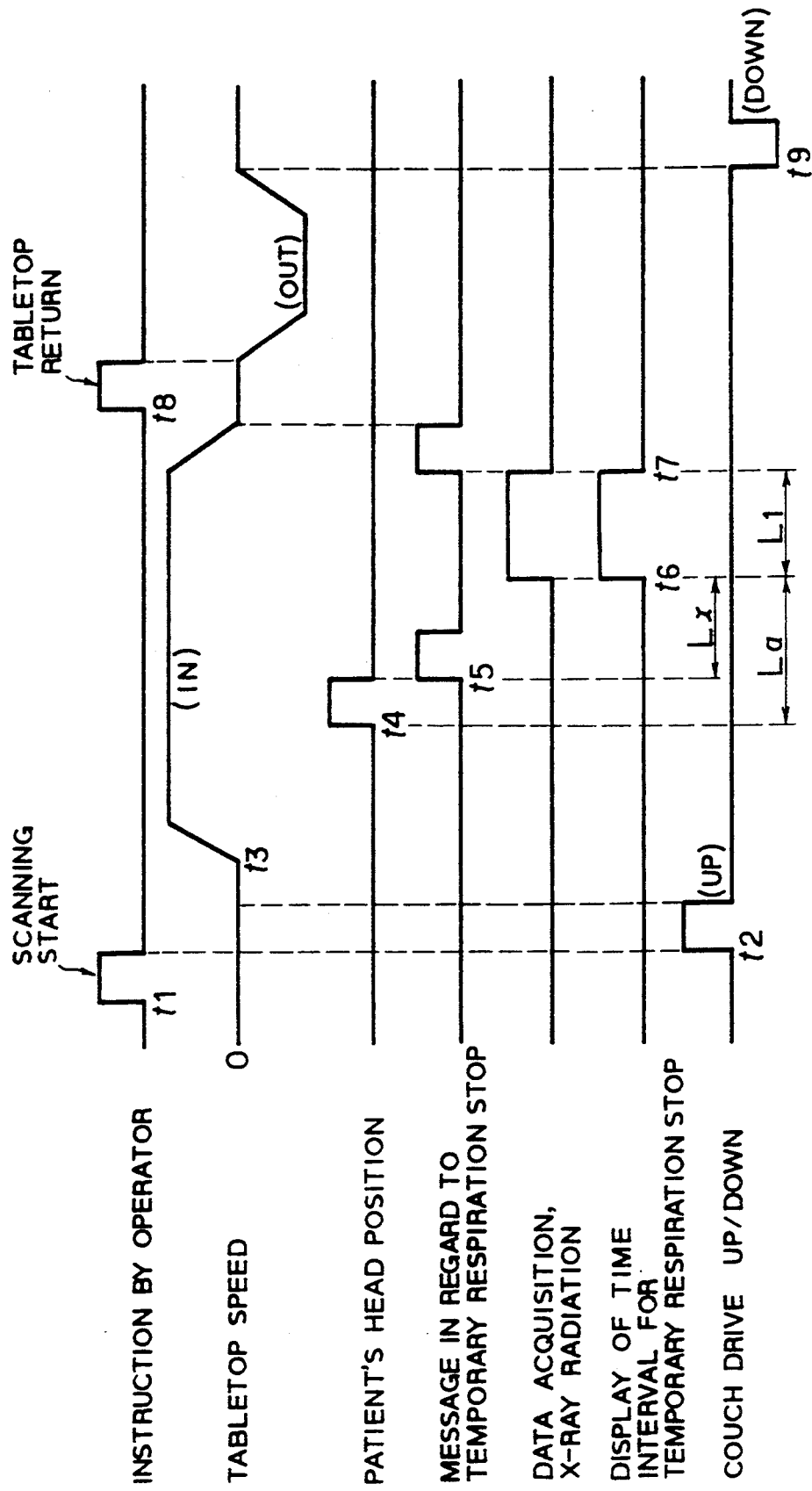
FIG. 13 shows a timing chart of the third embodiment.
Figure 14A:
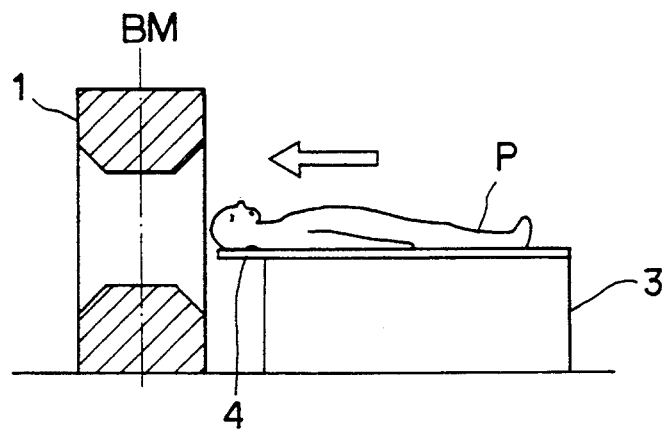
FIGS. 14A to 14D each show travel of a tabletop in the third embodiment.

In the same way as the first embodiment, scanning starts from its initial position shown in FIG. 14A and the tabletop 4 travels inward (see reference times t1 to t3 in FIG. 13).

Figure 14B:
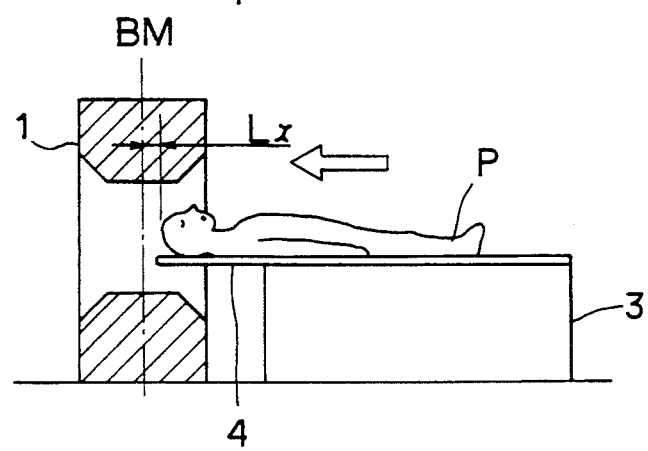
Figure 14C:
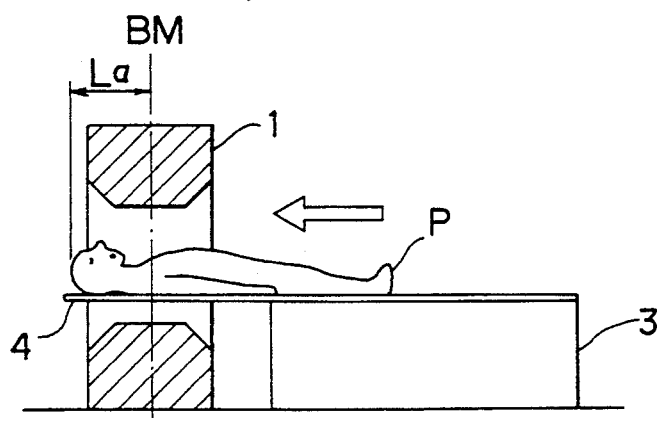
Figure 14D:
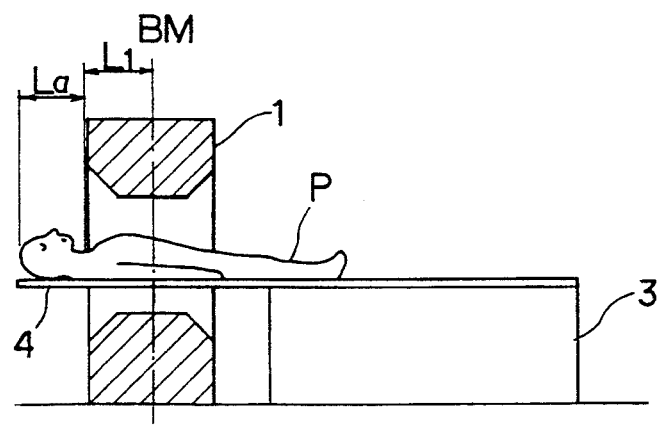

However, in this embodiment, when the top of the patient's head reaches the position of the photosensor 95 as shown in FIG. 14B (see a time t4 in FIG. 13), the arriving signal HD is returned to the main controller 30 (refer to Step 76c in FIG. 12 and Step 44a in FIG. 11). Therefore, the temporary discontinuation of respiration is instructed at a reference time t5 shown, and after a time interval corresponding to the non-scanning range La, the patient P arrives at its scan-start position, shown in FIG. 14C. Thus, the scan-start signal ST is returned to the main controller 30 (refer to Step 79 in FIG. 12 and Step 45 in FIG. 11), X-ray scanning and data acquisition for CT images beginning at a reference time t6.

For the scanning, the voice message to stop the respiration temporarily is generated at a proper time t5 before the scanning. And the time interval for the temporary discontinuation of respiration is also displayed and counted down with the scanning time.

After this, the processing is performed on the same way as the first embodiment.

As apparent from the above, body positioning pads used in the first and second embodiments are unnecessary for this scanner. So the tabletop 4 is more simplified and the operation of patient's body positioning is almost nothing. An operator can perform scanning directly after patients lie down on the couch, thus omitting the scan positioning procedure of the prior art. The same advantages described before are also acquired. In particular, a larger reduction in scanning time is accomplished.

In this embodiment, the photosensor 95 may be attached at the X-ray beam position BM in the gantry 1 (i.e., Lx=0) if necessary.

Recognizing means of the present invention for this embodiment are formed from the photosensor 95, Steps 44a, 44b, 45, 46, 50 and 51 in FIG. 11, and Steps 76a to 76e and 79 to 82 in FIG. 12.

A fourth embodiment of the present invention will now be described according to FIG. 15. This embodiment relates to a variation for the designation of a scan range under scanning.

Figure 15:
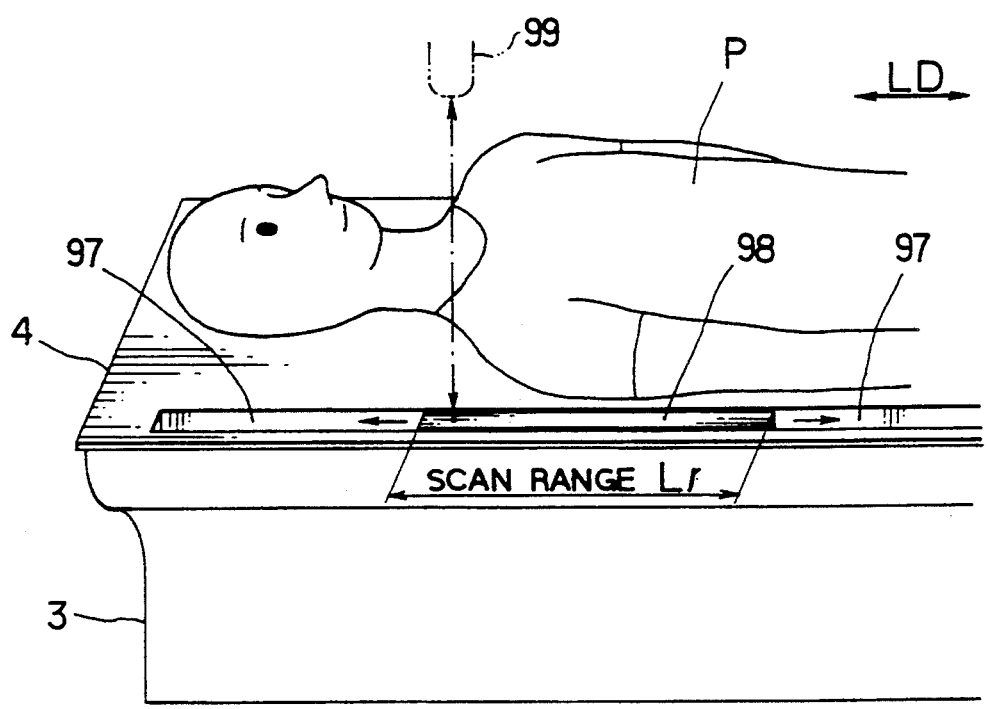
FIG. 15 shows an X-ray CT scanner of a fourth embodiment according to the present invention.

As shown in FIG. 15, a slit 97 is formed at one side along the body axis direction LD on the tabletop 4. There is a slider 98, serving as a rod means of the present invention, slidably inserted in the slit 97. The slider 98 is formed into a rod having a square in cross section. The length Lr of the slider 98 corresponds to the scan range in the body axis direction LD. Therefore, an operator selects the length of a slider 98 and adjusts its position in the slit 97, according to factors such as patient's height and target scan fields. The range of the slider 98 in the direction LD is detected by a photosensor 99, corresponding to a detector of the present invention, attached on the gantry 1, using a difference in light beam reflection rate between the slit 97 and the slider 98, for example. An output signal from the photosensor 99 is supplied to the tabletop controller 33 and used for the processing at Steps 80 and 81 in FIG. 12.

Figure 10:
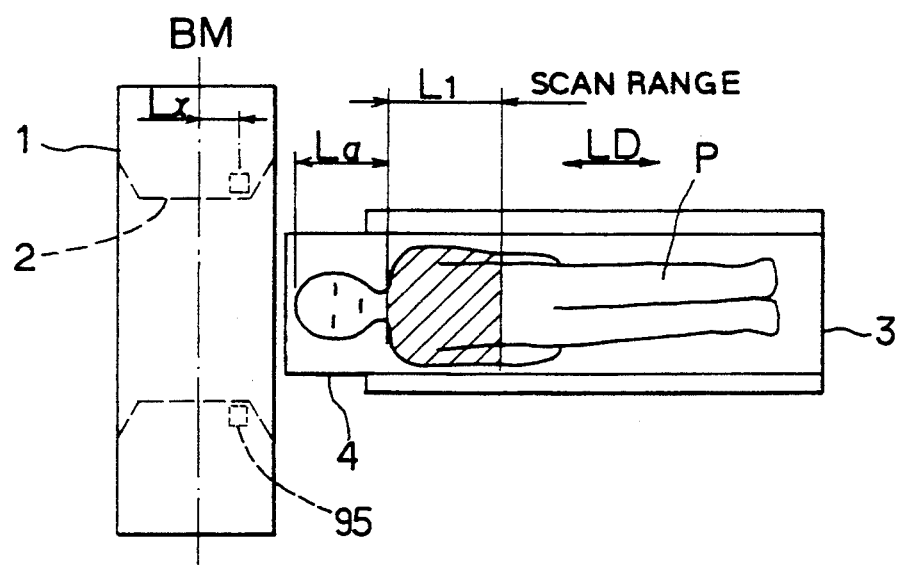
FIG. 10 represents a layout for a scan range in the third embodiment.

Thus, the slider 98 can decide the scan range L1(=Lr) shown as FIG. 10. In addition, the scan range L1 can be adjusted at the operator's will and is effective in visible and quick adjustment.

As one of varieties for the determination of the scan range, there is also a known mechanism comprising plural pointing devices such as switches to designate a scan range of a patient on the couch, the switches being arrayed along one side of the couch.

Further, the scan range is not limited to patient's lungs explained in the above embodiments. It is applicable to any part of a patient.

What we claim is:

1. An X-ray CT scanner having a gantry in which an X-ray tube rotatably incorporated therein radiates an X-ray beam upon a patient carried through an opening of the gantry and an X-ray detector rotatably incorporated in the gantry detects the X-ray beam transmitted through the patient, data of the X-ray beam thus-detected being used for reconstructing computed tomography images, the scanner comprising:

a couch having a tabletop on which the patient lies, the tabletop being movable along a longitudinal direction of the couch;

means for carrying the tabletop from a predetermined initial position of the tabletop in the longitudinal direction through the opening of the gantry;

means for detecting a standard position of the patient in the longitudinal direction at a radiation position of the X-ray beam in the gantry while the tabletop is being carried by the carrying means;

means for recognizing a scan range of the patient in response to detection information from the detecting means while the tabletop is being carried by the carrying means, said scan range being limited by a start position and an end position in the longitudinal direction;

means for scanning the scan region of the patient by the X-ray beam radiated from the X-ray tube for obtaining the data of the computed tomography images in response to information notifying the scan range recognized by the recognizing means; and means for reconstructing the computed tomography images using the data of the X-ray beam detected by the X-ray detector.

2. The X-ray CT scanner according to claim 1, further comprising means for positioning the patient body on the couch, wherein the standard reference position is a position in the longitudinal direction that is indirectly specified by the body positioning means.

3. The X-ray CT scanner according to claim 2, wherein said body positioning means consists of pads placed on the couch, the pads being able to be touched by the shoulders of the patient.

4. The X-ray CT scanner according to claim 3, wherein said pads are fixed on the tabletop.

5. The X-ray CT scanner according to claim 4, wherein said detection mechanism includes a sensor means detecting a position of the pads at the X-ray beam position and said determining mechanism has a first determining mechanism for determining arrival of the start position of the scan range at the X-ray beam position on the basis of information from the sensor means and a second determining mechanism for determining travel of the tabletop from the start position to the end position of the scan range.

6. The X-ray CT scanner according to claim 3, wherein said pads are movable along the longitudinal direction on the tabletop.

7. The X-ray CT scanner according to claim 6, wherein said detection mechanism includes a sensor means detecting a position of the pads at the X-ray beam position and said determining mechanism has a first determining mechanism for determining arrival of the start position of the scan range at the X-ray beam position on the basis of information from the sensor means and a second determining mechanism for determining travel of the tabletop from the start position to the end position of the scan range.

8. The X-ray CT scanner according to claim 7, wherein said first and second determining mechanisms include a mechanism to measure either one of a travel distance of the tabletop and a required time in travel of the tabletop and to calculate the start and end positions using the measured results.

9. The X-ray CT scanner according to claim 7, wherein said recognizing means further has a mechanism for generating start information and end information each corresponding to the start position and the end position of the scan range.

10. The X-ray CT scanner according to claim 9 further comprising means for automatically stopping travel of the tabletop in response to the end information generated by the generating mechanism.

11. The X-ray CT scanner according to claim 10, further comprising means for automatically returning the tabletop to the predetermined initial position after the tabletop was stopped by the stopping means.

12. The X-ray CT scanner according to claim 11, further comprising means for lowering the tabletop automatically after the tabletop is returned by said returning means and for lifting the tabletop automatically before the tabletop is carried by the carrying means.

13. The X-ray CT scanner according to claim 10, further comprising means for automatically returning the tabletop to the predetermined initial position in response to an operator's manual instruction after the tabletop was stopped by the stopping means.

14. The X-ray scanner according to claim 13, further comprising means for lowering the tabletop automatically after the tabletop is returned by the returning means and for lifting the tabletop automatically before the tabletop is carried by the carrying means.

15. The X-ray CT scanner according to claim 10, further comprising means for lowering the tabletop automatically after the tabletop is returned by the returning means and for lifting the tabletop automatically before the tabletop is carried by the carrying means.

16. The X-ray CT scanner according to claim 9, further comprising means for informing the patient to begin temporary discontinuation of respiration under scanning performed by the scanning means.

17. The X-ray CT scanner according to claim 16, wherein said informing means has a voice generator generating a message in regard to the temporary discontinuation of respiration in response to the start and end information.

18. The X-ray CT scanner according to claim 16, wherein said informing means has a time display unit displaying a maximum of a time interval required for the scanning in response to the start information and counting down the displayed time values.

19. The X-ray CT scanner according to claim 18, wherein said time display unit is placed on the gantry.

20. The X-ray CT scanner according to claim 16, wherein said informing means has a voice generator generating a message in regard to the temporary discontinuation of respiration and a time display unit displaying a maximum of a time interval required for the scanning and counting down the displayed time values.

21. The X-ray CT scanner according to claim 9, further comprising means for informing the patient to begin temporary discontinuation of respiration under scanning performed by the scanning means.

22. The X-ray CT scanner according to claim 21, wherein said informing means has a voice generator generating a message in regard to the temporary discontinuation of respiration in response to the start and end information.

23. The X-ray CT scanner according to claim 21, wherein said informing means has a time display unit displaying a maximum of a time interval required for the scanning in response to the start information and counting down the displayed time values.

24. The X-ray CT scanner according to claim 23, wherein said time display unit is placed on the gantry.

25. The X-ray CT scanner according to claim 21, wherein said informing means has a voice generator generating a message in regard to the temporary discontinuation of respiration and a time display unit displaying a maximum of a time interval required for the scanning and counting down the displayed time values.

26. The X-ray CT scanner according to claim 2, wherein said recognizing means further has a forming mechanism for forming profile data determining the start position and the end position of the scan range along the longitudinal direction, said profile data being formed in parallel with the scan carried out by the scanning means and using the data of the X-ray beam detected by the X-ray detector.

27. The X-ray CT scanner according to claim 2, wherein said body positioning means consists of marks located on the couch.

28. The X-ray CT scanner according to claim 1, wherein said recognizing means has a detection mechanism for detecting the start position at the radiation position of the X-ray beam in the gantry and a determining mechanism for determining the scan range based on detection information from the detection mechanism.

29. The X-ray CT scanner according to claim 28, wherein said standard position is a top of the patient's head.

30. The X-ray CT scanner according to claim 29, wherein said determining mechanism has a first count unit for counting a distance from the top of the head to the start position of the scan range and a second count unit for counting a distance from the start position to the end position of the scan range.

31. The X-ray CT scanner according to claim 30, wherein said recognizing means further comprises a mechanism for generating start information and end information each corresponding to the start position and the end position of the scan range.

32. The X-ray CT scanner according to claim 31, further comprising means for automatically stopping travel of the tabletop in response to the end information generated by the generating mechanism.

33. The X-ray CT scanner according to claim 32, further comprising means for automatically returning the tabletop to the predetermined initial position after the tabletop was stopped by the stopping means.

34. The X-ray CT scanner according to claim 32, further comprising means for lowering the tabletop automatically after the tabletop is returned by said returning means and for lifting the tabletop automatically before the tabletop is carried by the carrying means.

35. The X-ray CT scanner according to claim 32, further comprising means for automatically returning the tabletop to the predetermined initial position in response to an operator's manual instruction after the tabletop was stopped by the stopping means.

36. The X-ray CT scanner according to claim 35, further comprising means for lowering the tabletop automatically after the tabletop is returned by the returning means and for lifting the tabletop automatically before the tabletop is carried by the carrying means.

37. An X-ray CT scanner having a gantry in which an X-ray tube rotatably incorporated therein radiates an X-ray beam upon a patient carried through an opening of the gantry and an X-ray detector rotatably incorporated in the gantry detects the X-ray beam transmitted through the patient, data of the X-ray beam thus detected being used for reconstructing computed tomography images, the scanner comprising:

a couch having a tabletop on which the patient lies, the tabletop being movable along a longitudinal direction of the couch;

means for carrying the tabletop from a predetermined initial position of the tabletop in the longitudinal direction through the opening;

means for recognizing a scan range of the patient in the longitudinal direction while the tabletop is being carried by the carrying means for obtaining the computed tomography images, the scan range corresponding to a desired predetermined scanning region;

means for scanning the scan region of the patient by the X-ray beam radiated from the X-ray tube for obtaining the data of the computed tomography images in response to information notifying the scan range recognized by the recognizing means; and means for reconstructing the computed tomography images using the data of the X-ray beam detected by the X-ray detector;

said recognizing means having a slit formed at one end along the longitudinal direction on the tabletop, the slit being inserted by a rod means whose longitudinal length corresponds to the scan range, the rod means having a different physical property from the slit, and a detector to detect each point on the longitudinal length of the rod means.

38. The X-ray CT scanner according to claim 37, wherein said rod means is slidable along the longitudinal direction of the slit.

39. An X-ray CT scanner having a gantry in which an X-ray tube rotatably incorporated therein radiates during scanning an X-ray beam upon a patient carried through an opening of the gantry, and having means for reconstructing computed tomography images using data of the X-ray beam received through the patient, the scanner comprising:

means for generating a signal indicative of a start and an end of the scanning; and means for informing the patient of temporary discontinuation of respiration required for the scanning on the basis of the signal from the signal generating means.

40. The X-ray CT scanner according to claim 39, wherein said informing means has a voice generator generating a message in regard to the temporary discontinuation of respiration in response to the start and end signal.

41. The X-ray CT scanner according to claim 39, wherein said informing means has a time display unit displaying a maximum of a time interval required for the scanning in response to the start signal and counting down the displayed time values.

42. The X-ray CT scanner according to claim 41, wherein said time display unit is placed on the gantry.

43. The X-ray CT scanner according to claim 39, wherein said informing means has a voice generator generating a message in regard to the temporary discontinuation of respiration and a time display unit displaying a maximum of a time interval required for the scanning and counting down the displayed time values.

* * * * *